Figure 1:
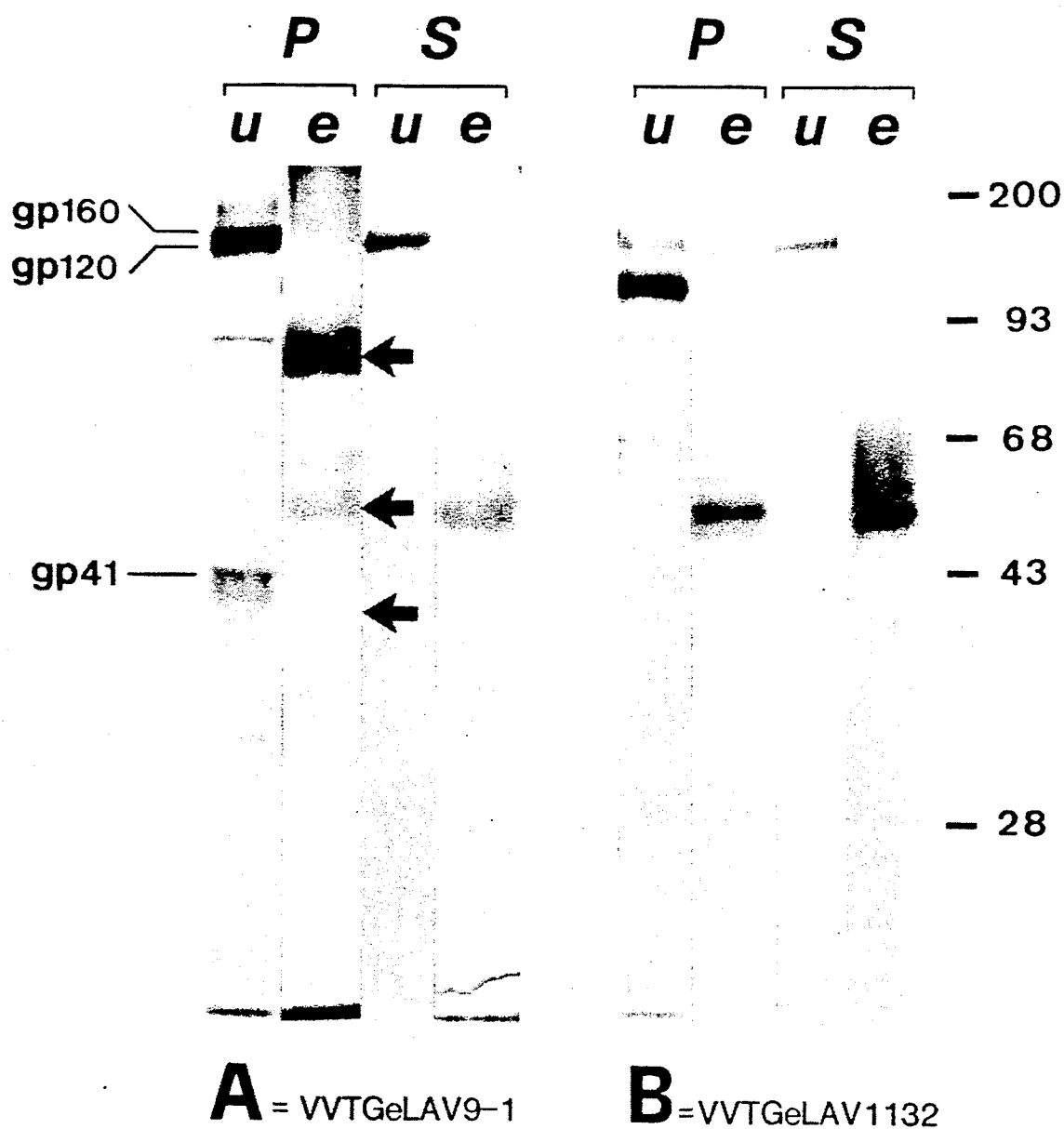

United States Patent [19]

Kieny et al.

[11] Patent Number: 5,169,763
[45] Date of Patent: Dec. 8, 1992

[54] VIRAL VECTOR CODING GLYCOPROTEIN OF HIV-1

[75] Inventors: Marie-Paule Kieny; Guy Rautmann, both of Strasbourg; Jean-Pierre Lecocq, Reichstett; Simon W. Hobson, Montigny-le-Bretonneux; Marc Girard, Paris; Luc Montagnier, Le Plessis-Robinson, all of France

[73] Assignee: Transgene S.A., Institut Pasteur, France

[21] Appl. No.: 765,413

[22] Filed: Sep. 24, 1991

Related U.S. Application Data

[63] Continuation of Ser. No. 143,079, filed as PCT/FR87/00116, Apr. 8, 1987, published as WO 87/06260, Oct. 22, 1987, abandoned.

[30] Foreign Application Priority Data

Apr. 8, 1986 [FR] France .................. 86 05043
Oct. 29, 1986 [FR] France .................. 86 15106

[51] Int. Cl.$^5$ .................. C12N 15/49; C12N 15/86; C12N 5/10; C12P 21/02
[52] U.S. Cl. .................. 435/69.3; 435/5; 435/69.1; 435/69.7; 435/172.3; 435/240.2; 435/974; 435/320.1; 530/395; 930/221; 935/32; 935/34; 935/70
[58] Field of Search .................. 435/69.1, 69.3, 69.7, 435/240.2, 320.1; 530/395

[56] References Cited

U.S. PATENT DOCUMENTS 4,753,873  6/1988  Beltz .................. 435/172.3

FOREIGN PATENT DOCUMENTS 2173804  10/1986  United Kingdom .

OTHER PUBLICATIONS

Anilionis, et al. Comp Immunol Microbiol Infect Dis 5:27–32, 1982.
Langford, et al. J. Cell Biochem Suppl 10A 1986, p. 48.
Crowl et al. Cell 41:979–986, 1985.
Stephens, E. B. et al. Cell (1986), vol. 47, 1053–1059.
H. Bialy, Bio/Technology, vol. 4, No. 3, Mar. 1986 "IL-2 crystals, TNF tests and AIDS vaccines", p. 166, col. 2.
S. Chakrabarti et al, Nature, vol. 320, Apr. 10, 1986, "Expression of the HTLV-III envelope gene by a recombinant vaccinia virus", pp. 535–537.
S. L. Hu et al., Nature, vol. 320, Apr. 10, 1986, "Expression of AIDS virus envelope gene in recombinant vaccinia viruses", pp. 537–540.
M. P. Kieny et al., Bio/Technology, vol. 4, No. 9, Sep. 1986, "AIDS virus env protein expressed from a recombinant vaccinia virus" pp. 790–795.
R. Sanchez-Pescador et al., Science, vol. 227, Feb. 1, 1985, "Nucleotide sequence and expression of an AIDS-associated retrovirus (ARV-2)", pp. 484–492.
L. A. Lasky et al., Science, vol. 233, Jul. 11, 1986, "Neutralization of the AIDS retrovirus by antibodies to a recombinant envelope glycoprotein", pp. 209–212.
M. P. Kieny et al., Nature vol. 312, No. 5990, Nov. 8, 1984, "Expression of rabies virus glycoprotein from a recombinant vaccinia virus", pp. 163–166.

Primary Examiner—Richard A. Schwartz
Assistant Examiner—Johnny F. Railey, II
Attorney, Agent, or Firm—Finnegan, Henderson, Farabow, Garrett & Dunner

[57] ABSTRACT

A viral vector comprising at least a portion of the genome of the HIV virus, a gene coding gp160 glycoprotein of the envelope of the HIV virus, as well as the elements providing for the expression of the glycoprotein in cells, wherein the gp160 is expressed as a noncleavable protein.

33 Claims, 5 Drawing Sheets

VIRAL VECTOR CODING GLYCOPROTEIN OF HIV-1

This application is a continuation of application Ser. No. 07/143,079, filed as PCT/FR87/00116 Apr. 8, 1987, published as WO 87/06260, Oct. 22, 1987, now abandoned.

The present invention relates more especially to a vaccine designed for the prevention of AIDS.

The acquired immune deficiency syndrome (AIDS) is a viral condition which is now of major importance in North America, Europe and Central Africa.

Recent estimates suggest that approximately 1 million Americans may have been exposed to the AIDS virus. The affected individuals show severe immunosuppression and the disease is generally fatal.

The disease is most commonly transmitted by sexual contact, although people using narcotics intravenously also represent a high-risk group; on the other hand, a large number of individuals have been infected with this virus after receiving contaminated blood or blood products.

The causal agent of this condition is a retrovirus. Many animal conditions have been attributed to retroviruses, but it is only recently that it has been possible to describe retroviruses affecting man.

Whereas human T cell retroviruses (HTLV: human T leukemia virus) of types I and II have been implicated as the causal agent of certain T cell leukemias in adults, the retrovirus associated with lymphadenopathies (LAV virus), which is also known as HTLV III or AIDS-related virus (ARV), is now generally accepted as the agent responsible for AIDS.

The genome of the LAV retrovirus has been characterized very completely (Wain-Hobson et al., 1985; Ratner et al., 1985; Muesing et al., 1985; Sanchez Pescador et al., 1985), and data on the sequence indicate a very close relationship with the lentivirus group. Lentiviruses, the prototype of which is ovine Visna virus, are slowly progressing disease agents which typically show a prolonged incubation period. LAV and Visna virus share many similarities, especially in their tropism for nerve tissue.

As with other well known retroviruses, the three most important parts of the LAV genome have been designated gag, pol and env. The sequence of the env gene, including the sequence of the gp110 and of the gp41, exhibits characteristics which were expected of a transmembrane envelope glycoprotein, and the identity of the env protein precursor, gp160, consisting of the gp110 and the gp41, has been confirmed by direct amino acid sequencing.

Antibodies produced against the env protein gp160 and its cleavage products gp120 and gp41 are commonly detected in the serum of patients who have AIDS, and the env glycoprotein represents the major surface antigen of the AIDS virus.

The env protein is thus the most promising candidate for developing a vaccination strategy, and for this reason attention has been concentrated on this protein and on its coding sequence.

A large number of groups have reported the expression of the env protein in bacteria. However, the absence of glycosylation and post-translational structuring can impair the immunogenic power of the materials synthesized by such microorganisms.

For this reason, the present invention proposes using a viral vector as expression vector for the env protein, this viral vector enabling the protein to be expressed in an environment which will permit its glycosylation and its post-translational restructuring.

Thus, the present invention relates to a viral vector which contains all or part of the env gene of the virus responsible for AIDS.

Among the viral vectors which are usable, poxviruses should be mentioned more especially, and vaccinia virus (VV) in particular.

Vaccinia virus is a double-stranded DNA virus which has been very widely used throughout the world to control and eradicate smallpox. Recent technical developments have enabled this virus to be developed as a cloning vector, and live recombinant viruses have enabled foreign antigens to be expressed and have even enabled immunizations against different viral or parasitic diseases to be obtained.

Thus, several groups have recently demonstrated the use of recombinants of this type to express the influenza antigen, the hepatitis B antigen and the rabies glycoprotein, for immunization against these diseases (Smith et al., 1983; Panicali et al., 1983; Kieny et al., 1984).

The expression of a coding sequence for a foreign protein by vaccinia virus (VV) necessarily involves two stages:

1) the coding sequence must be aligned with a VV promoter and be inserted in a nonessential segment of the VV DNA, cloned into a suitable bacterial plasmid;

2) the VV DNA sequences situated on either side of the coding sequence must permit homologous recombinations in vivo between the plasmid and the viral genome; a double reciprocal recombination leads to a transfer of the DNA insert from the plasmid to the viral genome in which it is propagated and expressed (Panicali and Paoletti, 1982; Mackett et al., 1982; Smith et al., 1983; Panicali et al., 1983).

Naturally, the use of this type of vector frequently involves a partial deletion of the genome of the vector virus.

The present invention relates more especially to a viral vector which contains at least:
a part of the genome of a vector virus,
a gene coding for one of the glycoproteins (gp) of the envelope of the virus responsible for AIDS, and also the elements which provide for the expression of this glycoprotein in cells.

The invention also relates to the recombinant DNAs corresponding to the said viral vectors.

It is appropriate to point out that 3 glycoproteins (gp) may be counted in the envelope of the virus responsible for AIDS, designated by their mass in kD, namely the gp160, the gp120 and the gp41; the first, gp160, is, in fact, the precursor of the latter two proteins. These designations are not yet firmly established, and the gp41 is sometimes referred to as gp40 or gp42, but these 3 glycoproteins are completely identifiable as a result of the differences in mass, regardless of their designation.

Virus responsible for AIDS is understood, in particular, to designate the LAV virus, the HTLV III virus or ARV, and likewise possible point mutants or partial deletions of these viruses, as well as the related viruses.

In the part corresponding to the genome of the vector virus (as distinct from the virus responsible for AIDS), the viral vectors can be formed from the genome of a virus of any origin. However, it is preferable to use a part of the genome of a poxvirus, and more especially a part of the genome of vaccinia.

The conditions necessary for the expression of a heterologous protein in the vaccinia virus have been recorded above.

In general, to be capable of being expressed, the gene in question, for example the env gene, will have to be under the dependence of a promoter of a vaccinia gene; this promoter will generally be the 7.5 K protein promoter of vaccinia. In addition, the coding sequence will have to be cloned into a nonessential gene of vaccinia, which may possibly serve as a marker gene. In most cases, this will be the TK gene.

Among the glycoproteins of the envelope whose expression it is desired to achieve, the three proteins referred to above, namely the gp160, the gp41 and the gp120, should be mentioned.

In general, it will be preferable to achieve expression of the complete envelope gene, that is to say the env gene incorporating the signal sequence and the transmembrane sequence of this gene.

As a result of the first tests performed with a viral vector in which the gene coding for the total env protein was cloned, modifications of this gene were proposed in order to improve the immunogenicity of the expression products.

A considerable release of the env protein into the culture supernatants was observed (which release probably occurs in vivo, into the circulating fluids). This may be due to a poor attachment of the protein in the cell membrane; it is known, in addition, that the presentation of the antigens at the cell surface is very important for the induction of an immune response with the vaccinia system. It is hence proposed to modify the env gene so as to improve the anchoring of the glycoprotein in the cell membrane.

To this end, the env gene may be modified at its portion which codes for the transmembrane region, so as to replace the codon corresponding to an arginine by a codon corresponding to an isoleucine.

There is also a possibility of improving the anchoring by replacing and/or adding the transmembrane region of a heterologous virus, for example the transmembrane region of the gp of rabies virus, to the transmembrane region of the env protein.

Furthermore, there is the possibility that the protein is not satisfactorily assembled following its expression. In effect, the signal peptide is fairly atypical, and might impair the complete exportation of the protein. For this reason, it is proposed to replace and/or add a signal sequence which originates from a heterologous virus, for example the signal sequence of the gp of rabies virus.

Finally, the gp120, rather than the gp160, appears to be the species which is released by the cells. It may, on the one hand, provide a decoy for the immune system, and on the other hand, in keeping with recent data, become bound to the T4 cells, which might have the effect of inactivating the T4 cells or of making them appear foreign to the other T cells.

It may hence be advantageous to obtain a gp120 env protein which cannot be released. This is accomplished by modifying the env gene between the sequences coding for the gp120 and for the gp41, so as to eliminate the site for cleavage by proteases situated between the gp120 and the gp41, in particular by elimination of the REKR site.

In the plasmids according to the invention, at least one additional mutation is performed in a site corresponding to a KRR sequence situated 8 amino acids downstream from the REKR sequence. The gp160 thereby obtained is no longer cleaved.

The vectors according to the present invention also contain a sequence coding for the gp41 which is devoid of the sequence corresponding to its hydrophobic N-terminal peptide, which it is thought might be responsible for the syncitial power of the env protein, that is to say the capacity of the virus to cause cell fusion and to produce a giant cell or syncitium.

Finally, the present invention relates to viral vectors in which the extracytoplasmic and intracytoplasmic regions of the gp160 are fused in phase after deletion of the C-terminal hydrophobic peptide, thereby enabling secretion of the glycoprotein to be obtained.

In general, the viral vectors according to the invention contain a sequence coding for one of the following proteins:

$$\text{-S-gp120} \xrightarrow{\text{J}} \text{gp40-(tm)-}$$

S is signal peptide,
gp120 is the glycoprotein 120,
J denotes schematically the junction portion between the gp120 and the gp40 which is devoid of a site for cleavage by proteases,
gp40 is the glycoprotein 40,
tm is a transmembrane peptide
or alternatively for a protein of structure:

$$\text{- S - gp40 - tm}$$

or $$\text{- S - gp120 - tm}$$

The signal peptide and the transmembrane sequence can be those of the virus responsible for AIDS or can be heterologous, in particular can originate from the rabies virus or VSV or any virus having an envelope.

The gp40 can optionally be devoid of its hydrophobic N-terminal end.

The first (sic) invention relates mainly to the use of viral vectors for obtaining the glycoproteins encoded by the env gene of LAV virus in cell cultures. The cells in question are hence initially mammalian cells which have been infected by a viral vector according to the invention, or alternatively which may contain the corresponding recombinant DNA; among these cells, there should be mentioned, more especially, human diploid cells, from primary cultures as well as Vero cells. It is naturally possible to provide for other types of cells, as will emerge, moreover, from the examples below.

The glycoproteins thereby obtained can be used after purification for the production of vaccines.

It is also possible to provide for the direct use of the viral vectors according to the invention in order to perform a vaccination, the glycoproteins then being produced in situ and in vivo.

It is advantageous to provide for the combined use of several vaccinating agents, administered jointly or separately, especially the vaccinating agents corresponding to the vectors which separately express the gp120 and the gp40 subjected to the modification described above. For example, it may be advantageous to use jointly the vaccinating agents derived from the vectors 1136 and 1138 which will be described below.

Finally, the present invention also relates to the antibodies produced against the above glycoproteins, the antibodies being obtained by infection of a living organism with a viral vector as described above and recovery of the antibodies induced after a specified time.

The techniques employed for obtaining the glycoproteins, the cell cultures and the vaccination techniques are identical to those which are currently performed with known vaccines, and will not be described in detail.

The present invention will be more satisfactorily understood on reading the methods and examples which follow.

Five figures illustrate the examples:

FIG. 1 shows the action of endo-F on the proteins synthesized by the recombinants VVTGeLAV9$^{-1}$ and VVTGeLAV1132 and immunoprecipitated by means of an anti-LAV serum. In this figure, the molecular weights are given in kilodaltons and the labeling is as follows:

P, the cell pellet
S, the supernatant
u, the products obtained without treatment
e, the products obtained after treatment with endo-F.

Figure 2:
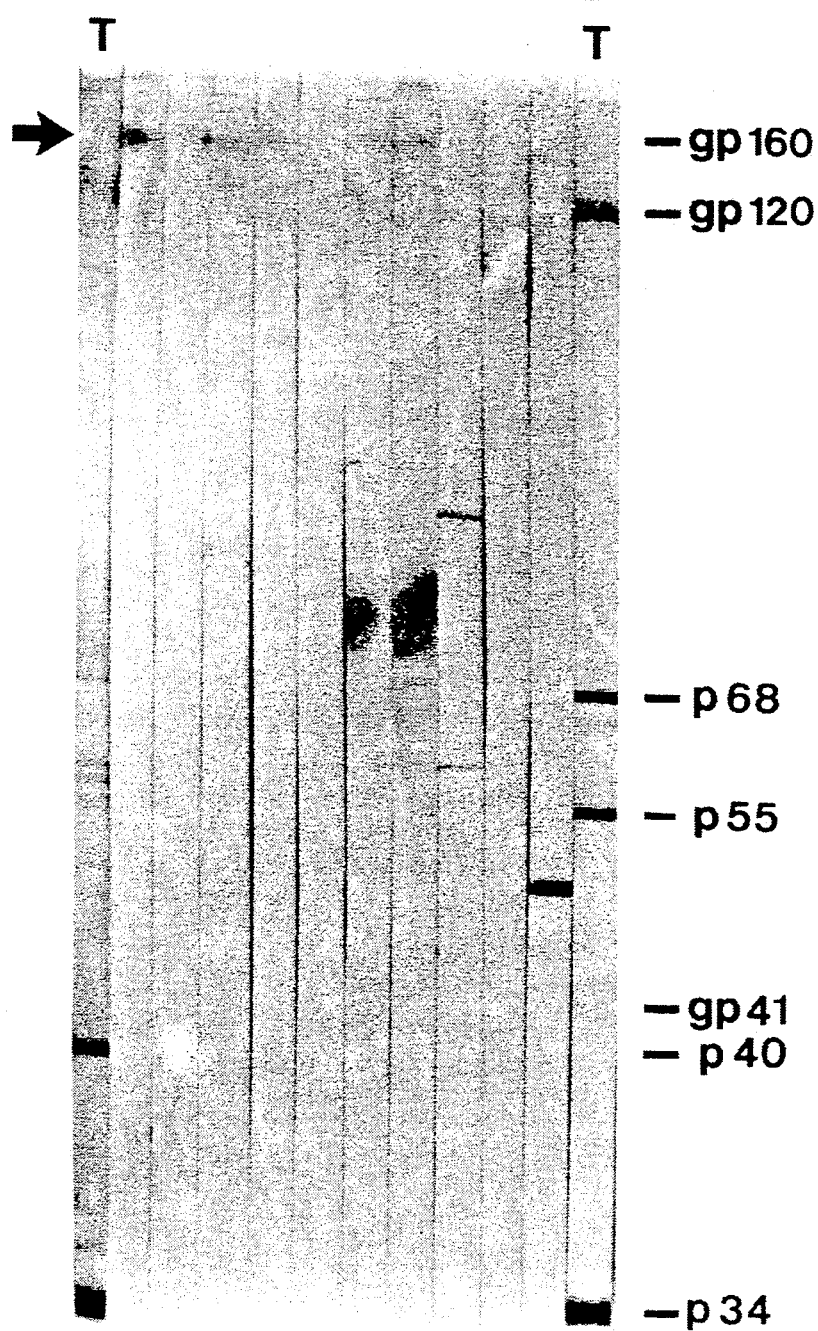

FIG. 2 shows the recognition of the proteins of the LAV virus by the sera of mice vaccinated with the recombinant VVTGeLAV9-1. In this figure, T denotes the cases where the serum used is that of a patient suffering from AIDS. The molecular weights are expressed in kilodaltons.

Figure 3:
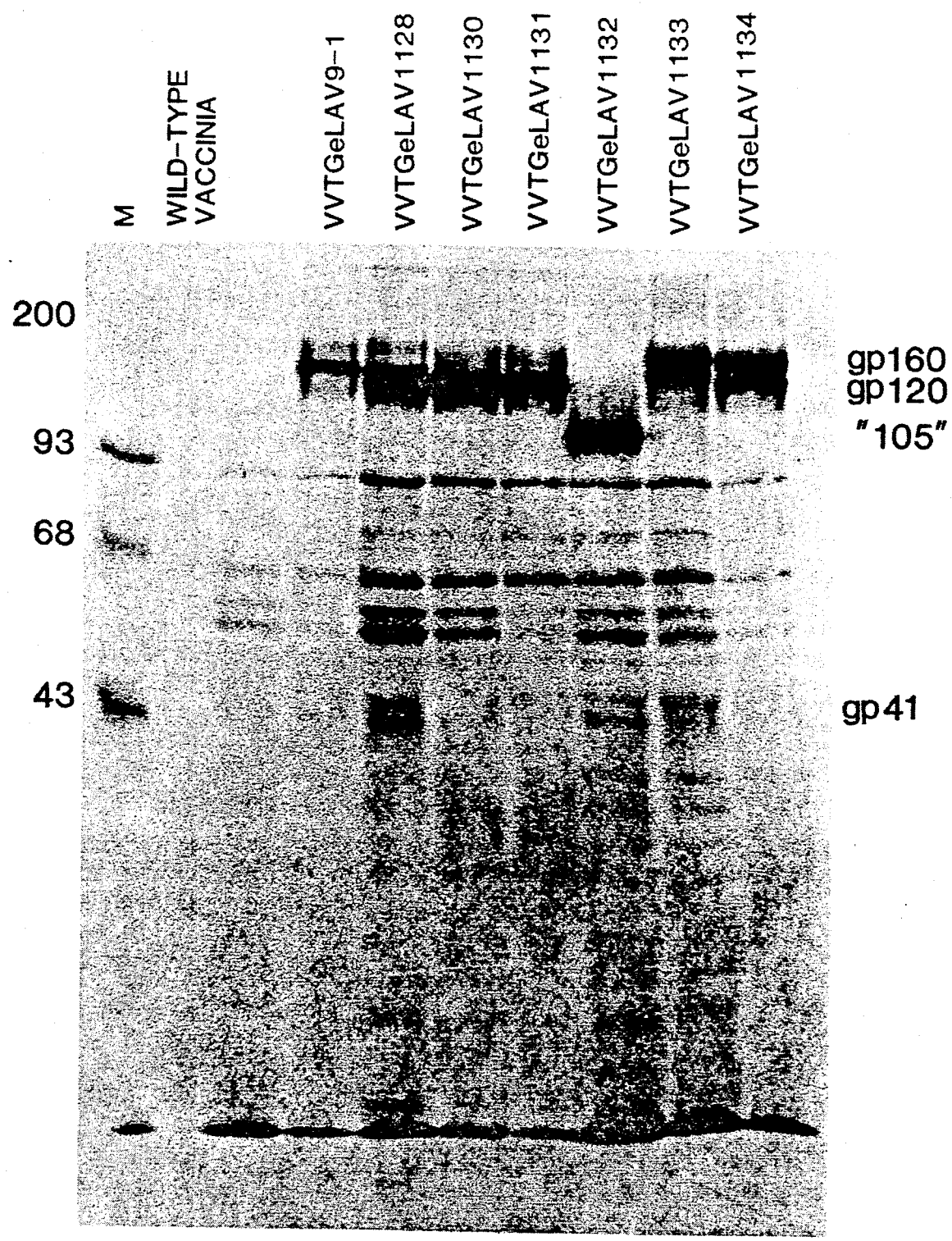

FIG. 3 shows the immunoprecipitation of the proteins synthesized by the recombinant vaccinia viruses bearing the env gene. In this figure, the molecular weights are in kilodaltons.

Figure 4:
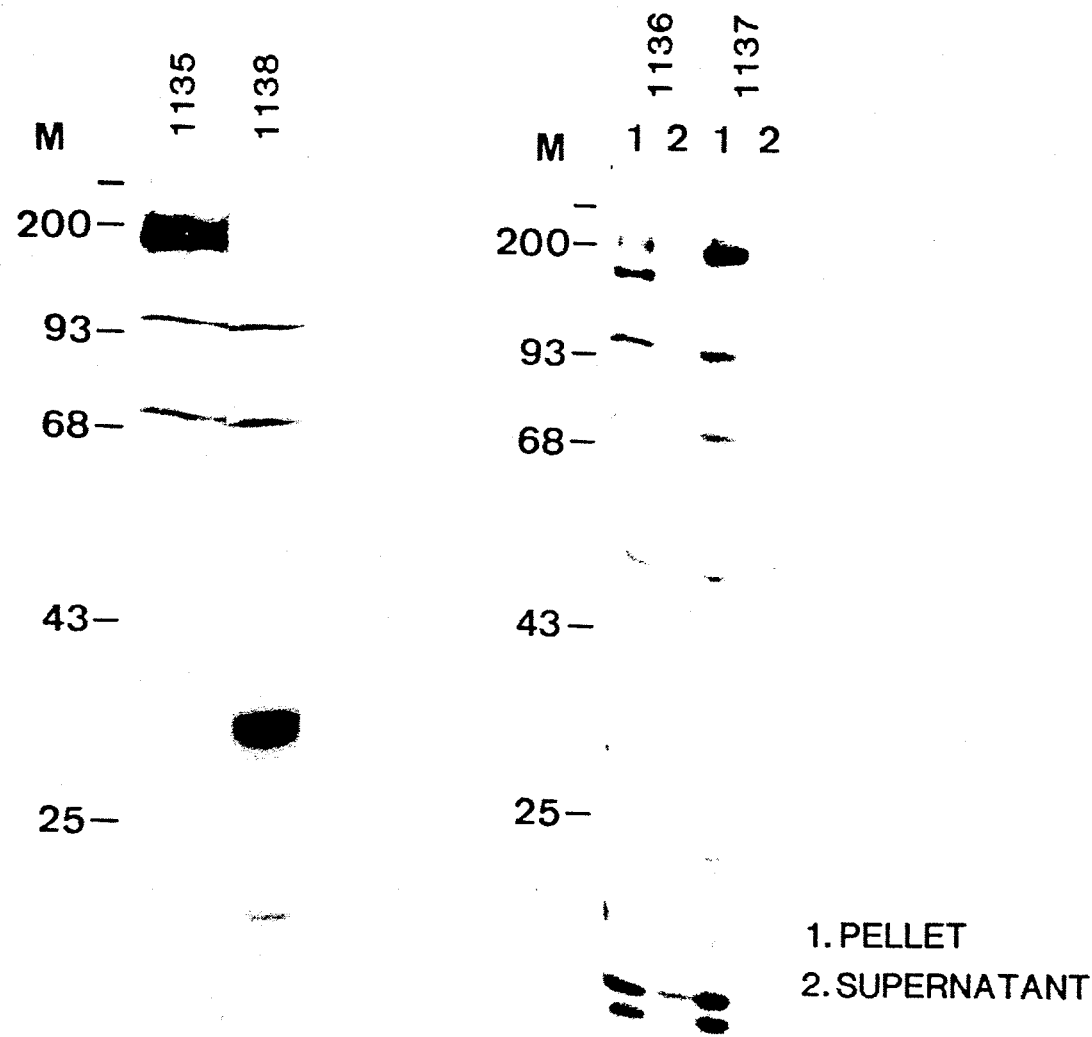

FIG. 4 shows an immunoprecipitation of the proteins synthesized by the recombinant viruses VV.TG.eLAV 1135, 1136, 1137 and 1138. The virus 1135 synthesizes a gp160 which does not appear in the culture supernatant. As regards the viruses 1136 and 1138, they produce proteins gp120 and gp40, respectively, associated with the cell pellet. The virus 1137 produces a slightly smaller protein than the virus 1135, with an MW in keeping with that expected.

Figure 5:
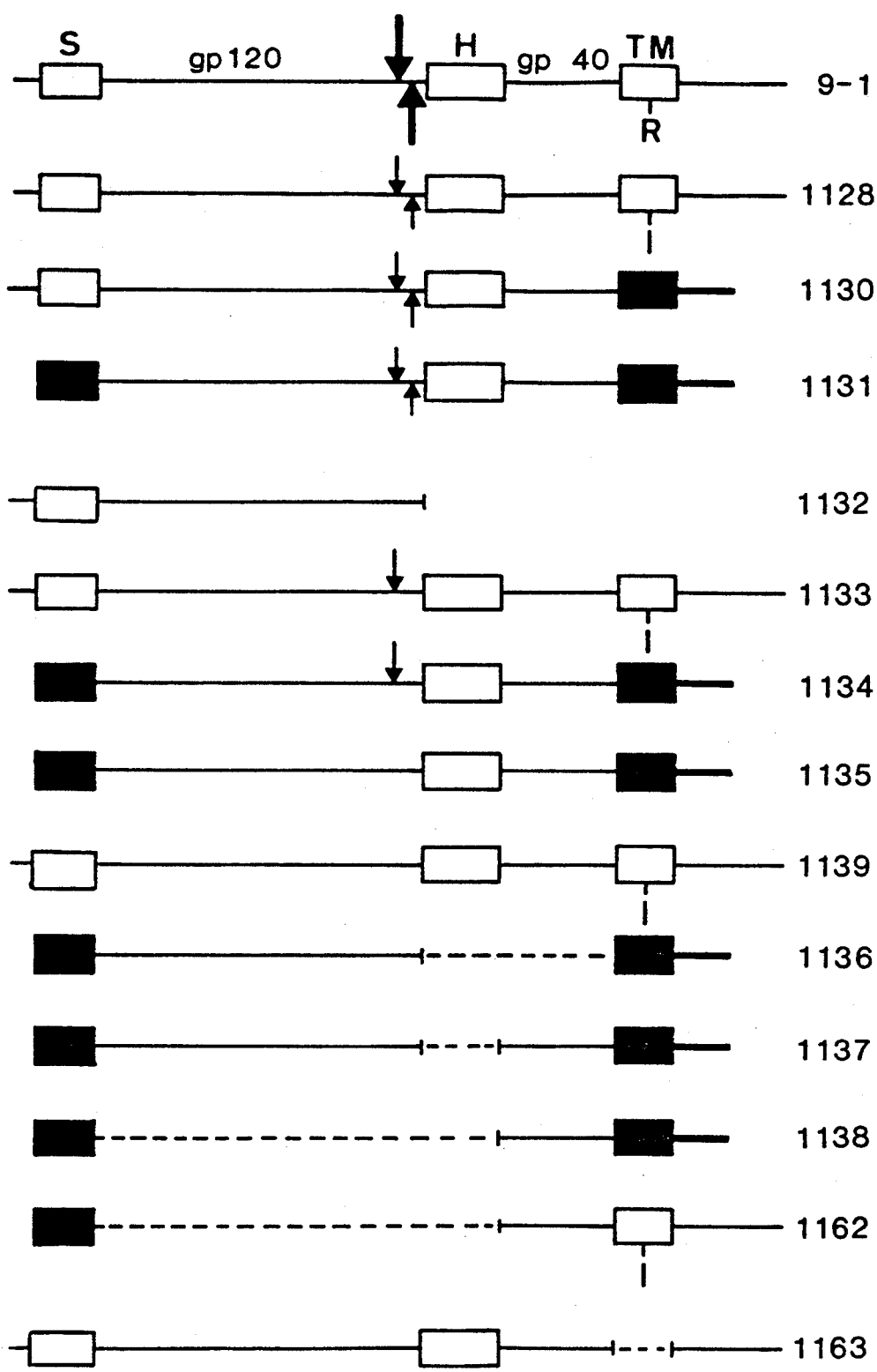

FIG. 5 shows the structure of the env proteins synthesized by the recombinant viruses described in the present invention.

S : a signal peptide
H : internal hydrophobic region
TM : transmembrane anchorage region
↑ : gp120/gp40 cleavage site
■ : sequence originating from the rabies glycoprotein.

METHODS

Cloning: Maniatis et al., 1982.

Enzymes: used according to the supplier's instructions.

Localized mutagenesis: method derived from Zoller and Smith, 1983.

Transfer into vaccinia: Kieny et al., 1984.

Only difference: human 143B cells replace the LMTK$^-$ cells.

Preparation of the Stock Virus

"Germ free" chicken primary cells are infected at 0.01 pfu/cell for 4 days at a temperature of 37° C. (MEM medium+5% NCS).

Purification of the Virus

The above stock virus is centrifuged for 15 minutes at 2500 rpm (Rotor GSA, Sorvall). The supernatant is set aside. The pellet is taken up in an RSB buffer (10 mM Tris-HCl ph 7.4, 10 mM KCl, 1 mM MgCl$_2$) for 15 minutes at 4° C. The suspension is ground in a Potter and then centrifuged for 15 minutes at 2500 rpm. The supernatant is added to the previous supernatant and a second grinding is then performed in the same manner.

All the supernatants are deposited on 10 ml of 36% (w/v) sucrose cushion (10 mM Tris pH 8). The suspension is centrifuged for 2 hours at 14,000 rpm (Rotor SW28, Beckman).

The pellet is taken up, broken up and replaced on a second identical cushion. The 2nd pellet is taken up in 5 ml of PBS and loaded onto a 20–40% sucrose gradient (10 mM Tris pH 8) (same rotor). The suspension is centrifuged for 45 minutes at 12,000 rpm.

The virus band is recovered. It is pelleted by centrifugation for 1 hour at 20,000 rpm. The pellet is taken up in 10 mM Tris pH 8.

Immunoprecipitations

BHK-21 cells are infected (dishes 3 cm in diameter, 10$^6$ cells per dish, cultured in G-MEM+10% FCS) at 0.2 pfu/cell for 18 hours. The medium is decanted and replaced by 1 ml of methionine-free medium and 10 μl of [$^{35}$S]methionine (Amersham) per dish.

An excess of non-radioactive methionine is added after 2 hours.

After the labeling, the infected cells are scraped off and centrifuged for 1 minute in an Eppendorf centrifuge, the supernatant and pellet fractions are separated, the pellet is washed once in PBS buffer, and then immunoprecipitation is carried out and gel electrophoresis performed (according to Lathe et al., 1980).

Endo-F Treatment

After immunoprecipitation of the labeled proteins with a serum of a patient suffering from AIDS, the protein A-sepharose fraction is taken up in:

0.2 M Na phosphate, pH 6.1
0.05% SDS
0.1% Nonidet P40
0.1% Beta-mercaptoethanol
0.1% EDTA pH 8 and boiled for 5 minutes to denature the proteins.

Incubation is performed for 20 hours at 37° C. with 4 units of endo-F per ml, followed by precipitation for 2 minutes in ice with 1/5 volume of 100% TCA. The pellet is washed 3 times with 80% acetone, the sample buffer is added and the mixture is loaded onto an SDS gel.

Antibody Assay by ELISA Test

LAV

Use of the ELAVIA test (Pasteur-Diagnostic) with a second sheep anti-mouse antibody linked to peroxidase.

Vaccinia

Plates having 96 flat-bottomed holes (NUNC) are incubated for 18 hours at 37° C. with 10$^7$ pfu of wild-type vaccinia virus in carbonate buffer. The plates are then saturated with 0.01% gelatin. The mouse sera are then adsorbed onto the plates and the remainder of the procedure is performed as for the LAV ELISA.

Readings taken at 492 nm.

EXAMPLE 1

Construction of the Hybrid Plasmids

The combined sizes of the different elements required for the transfer of the sequence coding for (sic) the env gene into the VV genome, and its subsequent expression are of the order of several kb. It was hence considered necessary to reduce to the minimum the size of the plasmid for replication in *E. coli* used for the construction work so-as to facilitate the necessary manipulations.

The HindIII fragment (Hin-J) of the VV genome contains the complete gene for thymidine kinase (TK), which has already been used previously to permit the exchange and recombination of DNA inserted in the VV genome (Mackett et al., 1982). It is important to note that the transfer of an insert into the TK gene of the VV genome creates a TK-deficient virus which can be selected. It was first necessary to produce a small-sized plasmid carrying a single HindIII site which could be used for the integration of the VV Hin-J fragment. In addition, it was necessary to remove the unnecessary restriction sequences from the plasmid so as to permit the following manipulations.

The construction was primed starting with plasmid pML2 (Lusky and Botchan, 1981), which is a vector derived from plasmid pBR322 by spontaneous deletion in which the segment between nucleotides 1089 and 2491 has been lost. First, the PstI sequence was removed by insertion of the AhaIII-AhaIII fragment of pUC8 (Vieira and Messing, 1982) between the two AhaIII sites of pML2, removing 19 base pairs. The "linker tailing" method (Lathe et al., 1984) was used to insert a HindIII linker between the NruI site and the EcoRI site, the latter being treated with S1, of this plasmid, the BamHI site being removed. This leads to a plasmid of 2049 base pairs carrying the functional beta-lactamase gene (which confers resistance to ampicillin) and containing in addition an origin of replication which is active in E. coli and a single HindIII restriction site.

This construction was referred to as pTG1H.

The Hin-J fragment of VV DNA carrying the TK gene has previously been cloned into a vector originating from pBR327 (Drillien and Spehner, 1983). This 4.6-kb fragment was recloned into the HindIII site of pTG1H. A clone was selected in which the TK gene is situated distally with respect to the gene coding for the resistance to ampicillin.

This construction pTG1H-TK was used as a vector in the following experiment.

The following stage was to isolate a VV promoter which could be used to control the expression of the sequence coding for the gene to be expressed. The promoter of an early gene coding for a protein of 7500 daltons (7.5 K) has already been successfully used for an identical purpose (Smith et al., 1983) and the isolation of this segment was hence undertaken.

The 7.5 K gene is situated on one of the smallest SalI fragments (Sal-S fragment) of the VV type WR genome (Venkatasan et al., 1981). Since the small fragments are cloned preferentially, a large proportion of the clones obtained by direct cloning of the DNA of VV type WR cut with SalI in plasmid pBR322 carries the Sal-S fragment. This fragment is transferred to the vector bacteriophage M13mp701 (see Kieny et al., 1983) by SalI digestion and religation, thereby leading to the phage M13TGSal-S.

In this clone, an ScaI site is present in immediate proximity to the initiation ATG of the 7.5 K gene. Downstream from the 7.5 K gene, there are situated single BamHI and EcoRI sites originating from the vector. The BamHI and ScaI sites are fused by a BglII linker 5'-CAGATCTG-3' after the ends generated by BamHI digestion have been filled in with the Klenow fragment of *E. coli*. This process removes the ScaI site but re-forms the BamHI site and shifts the single EcoRI site downstream. At the same time, the SalI (AccI) site downstream is removed, the SalI site upstream hence becomes unique.

This construction is referred to as M13TG 7.5 K.

Within the Hind-J (sic) fragment of VV DNA there are situated ClaI and EcoRI sites which are separated by approximately 30 base pairs (Weir and Moss, 1983). The 7.5 K promoter fragment present in M13TG7.5K is excised with AccI and EcoRI and cloned between the ClaI and EcoRI sites of pTG1H-TK to generate pTG1H-TK-P7.5K.

This construction leads to the transfer of the single BamHI and EcoRI sites from the M13 vector immediately downstream from the 7.5 K promoter sequence. These single BamHI and EcoRI sites are used in the following construction.

The polylinker segment of bacteriophage M13TG131 (Kieny et al., 1983) is excised with EcoRI and BglII and inserted between the EcoRI and BamHI sites of plasmid pTG1H-TK-P7.5K, generating pTG186-POLY. In this construction, 10 restriction sites are available for cloning a foreign gene under the control of P7.5K.

EXAMPLE 2

Construction of the Plasmid Carrying the Env Sequence

In order to obtain a sequence coding for env, the two proviral segments cloned into plasmids PJ19-6 and PJ19-13 are first assembled.

In order to provide for satisfactory translation of the env mRNA, the sequence of nucleotides around the presumed translation initiation site of the env gene was modified to match the consensus sequence of eukaryotic genes, this being achieved by a directed mutagenesis with an oligonucleotide in proximity to position 5767.

Plasmids PJ19-13 and PJ 19-6 contain HindIII fragments of the proviral genome of LAV, comprising nucleotides 1258 to 1698 and 1698 to 9173, respectively.

An EcoRI-KpnI fragment of PJ19-13 (containing the env initiation ATG) was inserted in phage M13TG130 and directed mutagenesis was performed with an oligonucleotide (sequence 5'CTCTCATTGTCACT-GCAGTCTGCTCTTTC), to introduce a PstI site upstream from the env translation initiation codon (position 5767) and in order to substitute the G at the 3-position by an A. The mutated fragment was then introduced between the EcoRI and KpnI sites of plasmid pTG1-POLY (which is a 2.1-kb mini-plasmid similar to pTG1H but which contains a polylinker segment of M13TG131).

The KpnI-HindIII fragment originating from PJ 1913 was then cloned into the same plasmid (between KpnI and HindIII, followed by a HindIII-XhoI fragment of PJ 19-6 (between HindIII and SalI), to generate a complete env coding sequence flanked by two PstI sites (plasmid pTG1124).

The introduction of these two PstI restriction sites permits easier manipulation of the DNA of the env gene in the subsequent stages of the construction. As stated above, the expression of a heterologous protein in vaccinia virus requires that the coding sequence be aligned with a promoter sequence of vaccinia and be inserted in a nonessential segment of the vaccinia DNA. This DNA situated on each side permits recombination with the vaccinia genome in vivo by a double reciprocal recombination, which transfers the coding sequence and the accompanying promoter into the vaccinia genome.

To this end, the PstI-PstI fragment mentioned above was cloned in the PstI site of pTG186-POLY. A plasmid designated pTG1125 is thereby obtained.

Plasmid pTG186-POLY can be generated from plasmid pTG188 digested with PstI and religated with T4 ligase.

Plasmid pTG188 was deposited on 20th June 1985 at the Collection Nationale de Cultures de Microorganismes (National Collection of Microorganism Cultures) of the Institut Pasteur, 28, rue du Docteur Roux, 75015 PARIS under the following number:

E. coli 5KpTG 188=No. I 458.

The transfer of the coding sequence of the env gene and the accompanying promoter into the vaccinia genome is accomplished as follows.

EXAMPLE 3

Cloning into Vaccinia Virus to Generate VV.TG.e LAV 9-1

The strategy described by Smith et al. (1983) rests on the exchange in vivo between a plasmid carrying an insert in the VV TK gene and the wild-type viral genome so as to inactivate the TK gene carried by the virus. The TK$^-$ viruses can be selected by plating on a cell line (TK-negative) in the presence of 5-bromodeoxyuridine (5BUDR) (Mackett et al., 1982). Thymidine kinase phosphorylates 5BUDR to 5'-monophosphate, which is then converted to triphosphate. This compound is an analog of dTTP and its incorporation in DNA blocks the correct development of the virus. A $TK^-$ virus can nevertheless replicate its DNA normally and it leads to visible viral plaques in a cell line which is also $TK^-$.

Vaccinia virus is propagated in the cytoplasm of infected cells rather than in their nucleus. For this reason, it is not possible to turn to account the machinery for replication and transcription of the host DNA, and it is necessary that the virion should possess the components for the expression of its genome. Purified VV DNA is noninfectious.

In order to generate the recombinants, it is necessary to perform simultaneously cellular infection with the VV virion and a transfection with the cloned DNA segment which is of interest. Nevertheless, the generation of the recombinants is limited to the small proportion of cells which are competent for transfection with DNA. For this reason, it was necessary to employ a strategy of indirect "congruence" to reduce the background of non-recombinant parent viruses. This was accomplished using as live infectious virus a temperature-sensitive (ts) mutant of vaccinia which is incapable of propagation at a nonpermissive temperature of 39.5° C. (Drillien and Spehner, 1983). When cells are infected with a ts mutant under nonpermissive conditions and transfected with the DNA of a wild-type virus, viral multiplication will occur only in the cells which are competent for the transfection and in which a recombination between the wild-type viral DNA and the genome of the ts virus has taken place; no virus will multiply in the other cells, despite the fact that they have been infected. If a recombinant plasmid containing a DNA fragment of vaccinia, such as pTG1125, is included in the transfection mixture, at the appropriate concentration, with the wild-type DNA, it is also possible to procure its participation in homologous recombination with the DNA of the vaccinia in the competent cells.

Primary cell monolayers of chick embryo fibroblasts (CEF) are infected at 33° C. with VV-Copenhagen ts7 (0.1 pfu/cell) and transfected with a calcium phosphate coprecipitate of the DNA of wild-type VV-Copenhagen virus (50 ng/$10^6$ cells) and the recombinant plasmid (50 ng/$10^6$ cells).

After incubation for 2 hours at a temperature which does not permit the growth of the ts virus (39.5° C.), the cells are incubated again for 48 hours at 39.5° C. Dilutions of $ts^+$ virus are used for reinfecting a monolayer of human 143B cells at 37° C., which are then incubated in the presence of 5BUDR (150 μg/ml . Various plaques of $TK^-$ virus are obtained from these cells which have received the recombinant plasmid, while the control cultures without a plasmid do not show visible plaques. The $TK^-$ viruses are then subcloned by a second selection in the presence of 5BUDR.

A correct double reciprocal recombination between the hybrid plasmid pTG1125 and the VV genome leads to the exchange of the TK gene carrying the insert with the TK gene of the virus, the recombinants thereby becoming $TK^-$.

The DNAs purified from the different $TK^-$ recombinant viruses are digested with HindIII and subjected to agarose gel electrophoresis. The DNA fragments are transferred to a nitrocellulose filter according to the technique described by Southern (1975). The filter is then hybridized with plasmid pTG1125 which has been nick-translated with $^{32}P$. After the filter is washed, the latter is fluorographed and 3.85-, 2.9- and 0.8-kb bands are visible on the autoradiograph when the vaccinia virus has incorporated the env gene of LAV. One of these recombinants, VV.TG. eLAV 9-1 was selected for the following studies.

EXAMPLE 4

Env Protein Synthesized from a Recombinant Vaccinia-LAV Virus

To demonstrate the expression of the env gene of LAV from the hybrid vaccinia virus, rodent cells, BHK21, which are cultured in a G-MEM medium +10% of fetal calf serum are infected with the same recombinant VV.TG. eLAV 9-1.

A fresh semi-confluent monolayer ($10^6$ cells is infected with 0.2 pfu/cell and incubated for 18 hours.

The medium is then removed and a medium having a low concentration of methionine (1 ml for $10^6$ cells), supplemented with 10 μl/ml of [$^{35}S$]methionine, is added. The cells are incubated at 37° C. and the labeled proteins are collected by centrifugation. After separation into pellet and supernatant, the proteins are incubated with a serum belonging to a patient suffering from AIDS. The proteins which react with the serum are recovered by adsorption on a protein A-Sepharose resin, and spread by electrophoresis on an SDS polyacrylamide gel and autoradiographed according to a technique described by Lathe et al., 1980. The autoradiographs show that the serum of the patient suffering from AIDS specifically binds three proteins in the infected cell extracts (the result is identical or similar to that obtained with other sera of patients). The apparent molecular weights of 160, 120 and 41 kD suggest equivalence with the gp160, gp120 and gp 41 bands identified by means of sera of patients suffering from AIDS in an authentic env glycoprotein preparation and in extracts of cells infected with the LAV virus. This observation, that three proteins are expressed from the recombinant vector which carries only the sequence coding for (sic) the env gene of LAV, supports the hypothesis that the gp120 and gp41 are generated by proteolytic cleavage of the primary translation product, gp160.

The sequence coding for env leads to a primary translation product of approximately 90 kD, whereas the env precursor obtained by the above method possesses an apparent molecular weight of approximately 160 kD. This difference is attributed to the presence of a very considerable amount of glycosylation. By digestion with endoglycosidase F, which removes the glycosyl groups, a good correlation could be demonstrated between the products obtained by the present invention and the predicted products (FIG. 1).

EXAMPLE 5

Demonstration of Anti-env Antibodies in Mice Vaccinated with the VV.TG.e LAV 9-1 Virus 5-week-old male Balb/c mice are vaccinated by subcutaneous injection of $5 \times 10^7$ pfu of VV.TV.e LAV 9-1 virus per animal. They receive a booster injection with the same dose after 2 weeks, and blood samples are withdrawn 1, 2 and 4 weeks after the booster. The presence of antibodies directed against determinants of LAV virus and of vaccinia virus in their sera is sought.

All the vaccinated animals give sera capable of reacting with vaccinia virus in an ELISA test. In contrast, the response in the ELISA test against LAV virus is weak and of low reproducibility. To improve the sensitivity of the tests, a "Western blot" technique was used. This method enables antibodies capable of reacting with the proteins of LAV virus to be demonstrated after these proteins have been denatured with SDS in an electrophoresis gel and transferred to a nitrocellulose membrane. In this experiment, the nitrocellulose membranes employed are those of the LAV-BLOT kit sold by Diagnostic-Pasteur and to which the proteins of LAV virus are already bound. These membranes are cut into strips and each strip is incubated with the serum of the vaccinated mice (1/20 dilution). A second antibody (sheep anti-mouse) linked to peroxydase enables the proteins of the LAV virus which have bound mouse antibodies to be visualized.

Several sera (12/27) give a specific reaction with a protein of molecular weight about 160 kD, corresponding to the gp160 of env (FIG. 2). In a certain number of sera, a reaction is also observed with the gp41 protein. It should be noted that the sera of a few mice produce signals in Western blot corresponding to unidentified proteins of the LAV virus preparation bound to the membranes.

EXAMPLE 6

Construction of pTG1128

This plasmid pTG1128 is identical to plasmid 1125 with the exception that the sequence coding for the transmembrane region has been mutated to replace the arginine by an isoleucine, this being in order to improve the attachment of the protein in the cell membrane.

The HindIII-BamHI fragment of pTG1124 containing the transmembrane region of env described in Example 2 is inserted into phage M13 TG131 after a HindIII-BamHI digestion. A phage M13 TG154 is thereby obtained.

A localized mutagenesis designed to replace the codon coding for arginine by a codon coding for isoleucine is then performed on this phage M13 TG154. For this purpose, the following oligonucleotide is used:

5' GGTTTAATAATAGTTTT 3'.

Phage M13 TG155 is thereby obtained, the sequences having been modified as follows:

|  | Gly | Leu | Arg | Ile | Val |
|---|---|---|---|---|---|
| Original sequence: | GGT | TTA | AGA | ATA | GTT |
| Mutated sequence: | GGT | TTA | <u>ATA</u> | ATA | GTT |
|  |  |  | Ile |  |  |

The BamHI-HindIII fragment thereby mutated is transferred from M13 TG155 into plasmid pTG1124 in equivalent sites, to give plasmid pTG1127 which reforms the env gene as above except that the arginine codon has been replaced by an isoleucine codon.

As described in Example 1, the PstI-PstI fragment of pTG1127 is cloned into the PstI site of plasmid pTG186POLY to give plasmid pTG1128.

EXAMPLE 7

Construction of Plasmid pTG1130

In this plasmid, the sequence coding for the transmembrane region of the rabies glycoprotein is fused with the beginning of the sequence coding for the transmembrane region of the env glycoprotein.

The transmembrane region of the rabies glycoprotein originates from a BamHI-PstI fragment of phage M13 TGRG151. This phage was previously described in EP-A-0 904887, published Feb. 1, 1984, in the name of the applicant. Phage M13 TGRG151 was obtained from plasmid pRC, described by Anilionis, et al., *Nature*, vol. 294, pages 275-278.

This fragment is cloned in phage M13 TG154 between the BamHI and PstI sites (see above example). The phage M13 TG156 is thereby obtained.

A localized mutagenesis is then performed on M13 TG156 in order to fuse in phase the env and rabies sequences with an oligonucleotide by forming a 5' GCTGTGGTATATAAAATATGTATTACT-GAGTG 3' loop

| Tyr | Leu | Lys | Ile | Phe |  | Gly | Lys | Tyr | Val |
|---|---|---|---|---|---|---|---|---|---|
| TAT | ATA | AAA | <u>ATA</u> | <u>TTC</u> | ----- | GGG | AAG | <u>TAT</u> | <u>GTA</u> |

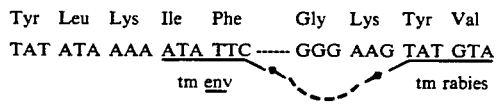

The phage M13 TG157 is thereby obtained.

The transmembrane (tm) region of the rabies glycoprotein which has just been fused with the env gene is then transferred into plasmid pTG1124.

For this purpose, the HindIII-BglII fragment of M13 TG157 is cloned into pTG1124 on which a HindIII-BamHI restriction has been performed (this destroys the BamHI and BglII sites).

The BglII site of M13 TG157 originates from the rabies gp fragment:

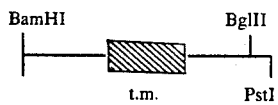

Plasmid pTG1126 is thereby obtained.

As above, PstI-PstI fragment of pTG1126 is cloned into the PstI site of pTG 186-POLY to give plasmid pTG1130.

EXAMPLE 8

Construction of pTG1131

The objective of the construction of this plasmid is to fuse the signal sequence of the env gene and the signal sequence of the rabies glycoprotein.

The signal sequence of the rabies glycoprotein is removed from plasmid pTG155 PRO in the form of a BglII-HindIII fragment, which is cloned into the PstI-HindIII sites of M13 TG130 by means of a single-stranded adaptor having the following sequence:

5' GATCTGCA 3'

The phage M13 TG158 is thereby obtained. Plasmid pTG155 PRO was described in EP-A-0 162757, published Nov. 27, 1985, in the name of the applicant.

The transfer of the env signal peptide into M13 TG158 is then carried out in order to fuse the latter with the gene coding for the signal peptide of the rabies glycoprotein.

For this purpose, the PstI fragment treated with S1 nuclease and then with Klenow and KpnI is cloned into M13 TG158 cut with HindIII and treated with Klenow/KpnI:

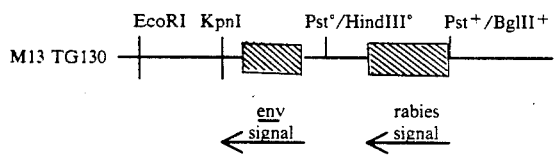

The plasmid (sic) M13 TG159 is thereby obtained.

The KpnI-PstI block of M13 TG159 is transferred into M13 TG131 to obtain plasmid (sic) M13 TG160.

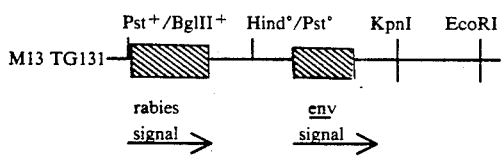

A localized mutagenesis on M13 TG160 enables the env and rabies glycoprotein sequences to be fused in phase (by forming a loop). This is achieved by means of the oligonucleotide

5' GACCCACAATTTTTCTGTAATAGGGAATTTCCCAAA 3'

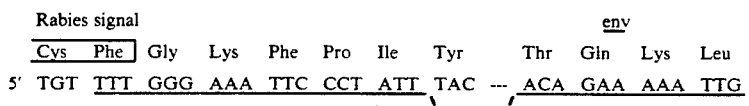

Phage M13 TG161 is thereby obtained.

The PvuII-KpnI fragment of M13 TG161 is then cloned into pTG1126 cut with EcoRI and treated with Klenow/KpnI (the PvuII site of M13 TG161 originates from M13 in the region situated upstream from the polylinker). This leads to plasmid pTG1129.

By cloning the PstI-PstI fragment of pTG1129 into plasmid pTG186-POLY cut with PstI, plasmid pTG1131 is obtained.

EXAMPLE 9

Preparation of Plasmid pTG1132

By cloning the PstI-PstI fragment of pTG1128 into the PstI site of M13 TG131, plasmid M13 TG162 is obtained.

A localized mutagenesis is then performed by means of the oligonucleotide

5'
ATTCCCACTGCTTAGTATTCATTCT-
GCACCACTC 3'

This enables a stop codon to be placed at the end of the gp120. The sequences obtained are as follows:

```
                    R   E   K   R   ↓
Original
sequence:  CAG AGA GAA AAA AGA   GCA GTG presumed cleavage site
                        of gp120

N   E   Y   ***
Mutated
sequence:  CAG AAT GAA TAC TAA  GCA GTG
```

The phage M13 TG168 is thereby obtained.

By recloning the PstI fragment of M13 TG168 into the PstI site of pTG186-POLY, plasmid pTG1132 is obtained.

EXAMPLE 10

Construction of Plasmid pTG1133

By localized mutagenesis on M13 TG162 by means of the following oligonucleotide:

5'
ATTCCCACTGCTTGGTGTTCATTCT-
GCACCACTC 3' a bacteriophage is obtained in which a potential cleavage site separating gp 120 and gp 40 has been destroyed. The modified sequences are as follows:

```
Original
sequence:  CAG AGA GAA AAA AGA ↑ GCA GTG
            R   E   K   R       A   V
                           cleavage site Mutated
sequence:  CAG AAT GAA CAC CAA    GCA
            N   E   H   Q
```

The phage M13 TG165 is thereby obtained.

By recloning the PstI-PstI fragment of M13 TG165 into pTG186-POLY at the PstI site, plasmid pTG1133 is obtained.

EXAMPLE 11

Construction of Plasmid pTG1134

By cloning the PstI-PstI fragment of pTG1131 into the PstI site of M13 TG131, the phage M13 TG163 is obtained.

A localized mutagenesis is performed on M13 TG163 in order to destroy the same cleavage site of the gp120 as above. For this purpose, the following oligonucleotide is used:

```
5'
  ATTCCCACTGCTTGATGTTCATTCT-
  GCACCACTC 3'
```

This enables the sequences to be modified in the following manner:

```
            R   E   K   R
Original
sequence:  CAG AGA GAA AAA AGA ↑ GCA GTG

Mutated
sequence:  CAG AAT GAA CAT CAA    GCA
            N   E   H   Q
```

Under these conditions, the phage M13 TG166 is obtained.

By recloning the PstI-PstI fragment of this phage M13 TG166 into the PstI site of pTG186-POLY, plasmid pTG1134 is obtained.

EXAMPLE 12

Immunoprecipitation of the Proteins Synthesized by the VV.TG. eLAV Recombinant Viruses By working as described above for plasmid pTG1125, the hybrid vaccinia vectors corresponding to the different plasmids prepared above are obtained.

These viral vectors will be referred to, respectively, as

VV.TG. eLAV 1128
VV.TG. eLAV 1130
VV.TG. eLAV 1131
VV.TG. eLAV 1132
VV.TG. eLAV 1133
VV.TG. eLAV 1134.

The proteins obtained as described above are tested by immunoprecipitation (FIG. 3).

For the virus 9-1, the group of immunoprecipitates reveals an immunoprecipitation corresponding to the gp160, the gp120 and the gp41.

The same applies for the virus 1128.

The virus 1130 also shows a gp160 and a gp120.

The protein corresponding to the gp41 has a slightly lower weight, due to the modification of its C-terminal end.

The virus 1131 shows a spectrum which is substantially identical to that obtained for the virus 1130.

The virus 1132 naturally does not show the protein corresponding to the gp41. The 105-kD protein present in the pellets is an isoform of the gp120 (different glycosylation).

As regards the virus 1133, this clearly shows the proteins 160, 120 and 41, but the bands corresponding to the proteins 120 and 41 are weaker than in the other spectra.

The same applies for the virus 1134, with which the gp41 also shows a lower molecular weight but for which it is clear that the cleavage took place with slower kinetics than those of the viruses VV.TG.1125 (9-1) to 1131.

EXAMPLE 13

Construction of Plasmid pTG1135

The kinetics of release performed on the VV.TG. eLAV1133 and 1134 viruses show that, although the kinetics of cutting between the gp120 and the gp40 are slower, the cleavage still takes place. The examination of the DNA sequence of the env gene reveals another potential cleavage site (KRR) 8 amino acids downstream from the first cleavage site. It may hence be important to mutate this second site so as to obtain a recombinant vaccinia virus which expresses only the gp160.

By localized mutagenesis on M13TG166 by means of the following nucleotide:

```
5'
  ATTCTGCACCACGT-
  GATTCTGTGCCTTGGTGGGT 3'
``` a phage is obtained in which the second cleavage site is modified. The modified sequences are as follows:

```
Original sequence:  GCA AAG AGA AGA GTG
                     A   K   R   R   V
                                   ↑
                               potential
                               cleavage site Mutated sequence:   GCA CAG AAT CAC GTG
                     A   Q   N   H   V
```

The PstI-PstI fragment of the phage obtained (M13TG181) is cloned into pTG186-POLY at the PstI site to generate plasmid pTG1135.

EXAMPLE 14

Construction of Plasmid pTG1139

The C-terminal portion of the env gene synthesized by the recombinant vaccinia vector VV.TG.eLAV1135 is a sequence derived from the rabies glycoprotein. It may hence appear to be useful also to have another recombinant in which this C-terminal portion was replaced by the C-terminal portion of the env gene of the LAV virus.

For this purpose, the same mutagenesis is performed on the phage M13TG165 as that performed (see Example 13) on the phage M13TG166, to generate the phage M13TG184.

The PstI-PstI fragment of M13TG184 is then recloned into plasmid pTG186-POLY to generate plasmid pTG1139.

EXAMPLE 15

Construction of Plasmid pTG1136

It would also be desirable to have a recombinant vaccinia virus which expressed only the gp120. This gp-120 will, in distinction to the case obtained with the VV.TG.eLAV1132 virus, be equipped with a C-terminal anchorage region.

For this purpose, the sequences corresponding to the gp40 in the phage M13TG181 are removed by localized mutagenesis using the following nucleotide:

5'
TGCACTCAGTAATACATACACGT-
GATTCTGTGCCTT 3'

This oligonucleotide enables the gp120 sequences (with the 2 modified cleavage sites) and the sequences of the transmembrane region of the rabies glycoprotein to be fused in phase.

| K | A | Q | N | H | V | V | F | Y | V | L | L |
|---|---|---|---|---|---|---|---|---|---|---|---|
| AAG | GCA | CAG | AAT | CAC | GTG | GTG | + TTC | TAT | GTA | TTA | CTG | gp120                                      rabies tm

Phage M13TG182 is thereby obtained. PstI-PstI fragment of M13TG182 is then inserted at the PstI site of pTG186POLY to generate plasmid pTG1136.

EXAMPLE 16

Construction of Plasmid pTG1137

The role of the hydrophobic region situated at the N-terminal portion of the gp40 is little known. This region of the env protein may be responsible for the power for inducing formation of syncitia.

It hence appears to be advantageous to produce a gp160 which does not contain this sequence.

For this purpose, the sequences upstream and downstream from the portion coding for this hydrophobic peptide in the phage M13TG181 are fused in phase by means of the following oligonucleotide:

5'
CAATAATTGTCTGGCCTGCACGT-
GATTCTGTGCCTT 3'

This enables the phage M13TG183 to be obtained by carrying out the fusion:

| AAG | GCA | CAG | AAT | CAC | GTG | GTG | + GTA | CAG | GCC | AGA | CAA |
|---|---|---|---|---|---|---|---|---|---|---|---|
| K | A | Q | N | H | V | V | | Q | A | R | Q | gp120                                  hydrophilic portion
                                       of the gp40

The PstI-PstI fragment of M13TG183 is recloned into the PstI site of pTG186-POLY to generate plasmid pTG1137.

EXAMPLE 17

Construction of Plasmid pTG1138

In addition to recombinant viruses which express the gp160 or the gp120, it may be useful to generate a recombinant vaccinia virus which expresses the gp40 alone.

For this purpose, the sequences coding for the signal peptide are fused with the sequences coding for the gp40 on the phage M13TG163, by means of the following nucleotide:

5'
CAATAATTGTCTGGCCTGAATAGG-
GAATTTCCCAAA 3'

This enables the phage M13TG180 to be generated, which contains the fusion:

| TGT | TTT | GGG | AAA | TTC | + CAG | GCC | AGA | CAA |
|---|---|---|---|---|---|---|---|---|
| C | F | G | K | F | Q | A | R | Q | signal                         gp40 (hydrophilic
of the                         portion)
rabies gp The PstI-PstI fragment of M13TG180 is inserted at the PstI site of pTG186-POLY to give plasmid pTG1138.

EXAMPLE 18

Construction of Plasmid pTG1162

As in the case of the gp160 (plasmid pTG1139), it may also be important to have a recombinant virus which expresses a gp40 in which the anchorage region and the intracytoplasmic region are the sequences of the env gene of the LAV virus, rather than the corresponding sequences of the rabies glycoprotein.

To obtain this, the HindIII-BglI fragment of M13TG180 is replaced by the HindIII-BglI fragment of M13TG165, generating phage M13TG190.

Plasmid pTG1162 is obtained by cloning the PstI-PstI fragment of the phage M13TG190 into the PstI site of plasmid pTG186-POLY.

EXAMPLE 19

Construction of Plasmid pTG1163

It also appears to be important to obtain a recombinant vaccinia virus which synthesizes a gp160 which is not cleaved and which is secreted into the medium. In effect, this protein might be used as a killed vaccine, in combination with adjuvants, or included in liposomes or ISCOMS [Morein et al., Nature (1984) 308, 5958 p.457-60].

For this purpose, the bacteriophage M13TG194, in which the sequences coding for the extracytoplasmic and intracytoplasmic regions are fused in phase in the bacteriophage M13 TG184, is constructed by means of the following oligonucleotide:

5'
TCCCTGCCTAACTCTATTTTTTATATAC-
CACAGCCA 3'

The PstI-PstI fragment of M13TG194 is then cloned at the PstI site of pTG186-POLY to give pTG1163.

The recombinant proteins thereby obtained, and especially the non-cleavable gp160, can be used in diagnostic kits for detecting potential antibodies present in the blood of patients who have been in contact with the virus. These tests can be carried out according to processes known to those versed in the art, for example by ELISA, RIPA or "Western blot" (immuno-imprinting).

These proteins can also be used for the production of hybridomas and monoclonal antibodies designed to detect the presence of virus in samples.

The different plasmids and M13 phages are described, in particular, in the following patent applications:
M13 TG131 : Kieny et al., 1983
M13 TGRG151: WO 83/04052
pTG155 PRO : FR 84 06499
M13 TG130 : Kieny et al., 1983.

The following plasmids were deposited on 16th November 1984 at the Collection Nationale de Cultures de Microorganismes [National Collection of Microorganism Cultures] of the Institut Pasteur, 28 rue du Dr. Roux, 75724 Paris, Cedex 15, France, and are described in Patent GB-A-84/29,099:
PJ 19-6 : CNCM No. 366-I
PJ 19-13 : CNCM No. 367-I.

Plasmid pTG1125 was deposited on 6th June 1986 in the same collection, in the form of a transformed bacterium E. coli 1106/pTG1125, under no. I-557.

REFERENCES

1. Drillien, R. and Spehner, D. (1983) Virology 131, 385-393.
2. Kieny, M. P., Lathe, R. and Lecocq, J. P. 1983. New versatile cloning and sequencing vectors based on bacteriophage M13. Gene 26 : 91-99.
3. Kieny, M. P., Lathe, R., Drillien, R., Spehner, D., Skory, S., Schmitt, D., Wiktor, T., Koprowski, H. and Lecocq, J. P. 1984. Expression of rabies virus glycoprotein from a recombinant vaccinia virus. Nature 312 : 163-166.
4. Lathe, R., Hirth, P., Dewilde, M., Harford, N. and Lecocq, J. P. 1980. Cell-free synthesis of biologically active heat-stable enterotoxin of *Escherichia coli* from a cloned gene. Nature 284 : 473-474.
5. Lathe, R., Kieny, M. P., Schmitt, D., Curtis, P. and Lecocq, J. P. (1984) J. Mol. Appl. Genet., vol. 2, 331-342.
6. Lathe, R., Kieny, M. P., Skory, S. and Lecocq, J. P. (1984) DNA, vol. 3, 173-182.
7. Lusky, M. and Botchan, M. (1981) Nature 293, 79-81.
8. Mackett, M., Smith, G. L. and Moss, B. 1982. Vaccinia virus : a selectable eukaryotic cloning and expression vector. Proc. Natl. Acad. Sci. USA. 79 : 7415-7419.
9. Maniatis, T., Fritsch, E. F. and Sambrook, J. 1982. Molecular cloning : a laboratory manual. Cold Spring Harbor Lab, N.Y.
10. Muesing, M. A., Smith, D. H., Cabradilla, C. D., Benton, C. V., Lasky, L. A. and Capon, D. J. 1985. Nucleic acid structure and expression of the human AIDS/lymphadenopathy retrovirus. Nature 313 : 450-458.
11. Messing and Vieras, Gene 19, 1982, p. 269-276.
12. Panicali, D. and Paoletti, E. 1982. Construction of poxviruses as cloning vectors : Insertion of the thymidine kinase gene from herpes simplex virus into the DNA of infectious vaccinia virus. Proc. Natl. Acad. Sci. USA. 79 : 4927-4931.
13. Panicali, D., Davis, S. W., Weinberg, R. L. and Paoletti, E. (1983) Proc. Natl. Acad. Sci. USA 80, 5364-5368.
14. Ratner, L., Haseltine, W., Patarca, R., Livak, K. J., Starcich, B., Josephs, S. F., Doran, E. R., Rafalski, J. A., Whitehorn, E. A., Baumeister, K., Ivanoff, L., Petterway Jr., S. R., Pearson, M. L., Lautenberger, J. A., Papas, T. S., Ghrayeb, J., Chang, N. T., Gallo, R. C. and Wong-Staal, F. Complete nucleotide sequence of the AIDS virus, HTLV-III. 1985. Nature 313 : 277-284.
15. Sanchez-Pescador et al., 1985. Science 227 : 484-492.
16. Smith, G. L., Mackett, M. and Moss, V. (1983) Nature 302, 490-495.
17. Smith, G. L., Murphy, B. R. and Moss, B. (1983) Proc. Natl. Acad. Sci. USA 80, 7155-7159.
18. Venkatesan, S., Baroudy, B. M. and Moss, B. (1981) Cell 125, 805-813.
19. Wain-Hobson, S., Sonigo, P., Danos, O., Cole, S. and Alizon, M. Nucleotide Sequence of the AIDS virus, LAV. 1985. Cell 40 : 9-17.
20. Weir, J. P. and Moss, B. (1983) J. Virol. 46, 530-537.
21. Zoller, M. J. and Smith, M. 1983. Oligonucleotide-directed mutagenesis of DNA fragments cloned into M13 vectors. In : Methods in Enzymology (Wu, Grossman, Moldave, eds.) 100 : 468-500.

We claim:

1. A viral vector, the genome of which comprises:
a functional origin of replication of a poxvirus;
a first DNA fragment encoding a non-cleavable gp160, consisting of gp120-gp140, derived from the natural gp160 of an HIV-1 virus, said non-cleavable gp160 being characterized in that it does not contain the amino acid sequence REKR originally found in the natural gp160;
a second DNA fragment encoding a signal peptide, said second DNA fragment being linked to the 5' end of said first DNA fragment; and
a promoter for expressing said DNA fragment in mammalian cells.

2. A viral vector according to claim 1, the genome of which comprises a first DNA fragment encoding a non-cleavable gp160 derived from the natural gp160 of the HIV-1 virus, said non-cleavable gp160 being characterized in that it does not contain the amino acid sequences KRR and REKR originally found in the natural gp160.

3. A viral vector according to claim 1, the genome of which comprises a first DNA fragment encoding a non-cleavable gp160 derived from the natural gp160 of the HIV-1 virus, said non-cleavable gp160 being characterized in that it comprises a 4-amino acid sequence other than REKR in place of the amino acid sequence REKR originally found in the natural gp160.

4. A viral vector according to claim 2, the genome of which comprises a first DNA fragment encoding a non-cleavable gp160 derived from the natural gp160 of the HIV-1 virus, said non-cleavable gp160 being characterized in that it comprises a 4-amino acid sequence other than REKR in place of the amino acid sequence REKR originally found in the natural gp160, and in that it comprises a 3-amino acid sequence other than KRR in place of the amino acid sequence KRR originally found in the natural gp160.

5. A viral vector according to claim 3, the genome of which comprises a DNA fragment encoding a non-cleavable gp160 derived from the natural gp160 of the HIV-1 virus, said non-cleavable gp160 being different from the natural gp160 in that the amino acid sequence REKR originally found in the natural gp160 is replaced by the amino acid sequence NEHQ.

6. A viral vector according to claim 4, the genome of which comprises a DNA fragment encoding a non-cleavable gp160 derived from the natural gp160 of the HIV-1 virus, said non-cleavable gp160 being different from the natural gp160 in that the amino acid sequences KRR and REKR are replaced respectively by the amino acid sequences QNH and NEHQ.

7. A viral vector according to claim 1, the genome of which comprises a first DNA fragment encoding a non-cleavable and soluble gp160 derived from the natural gp160 of the HIV-1 virus, said non-cleavable and soluble gp160 being different from the natural gp160 in that it does not contain the amino acid sequence REKR originally found in the natural gp160, and in that the transmembrane region originally found in the natural gp160 is deleted.

8. A viral vector according to claim 7, wherein said non-cleavable and soluble gp160 is different from the natural gp160 in that it comprises a 4-amino acid sequence other than REKR in place of the amino acid sequence REKR originally found in the natural gp160.

9. A viral vector according to claim 8, wherein said non-cleavable and soluble gp160 is different from the natural gp160 in that the amino acid sequence REKR originally found in the natural gp160 is replaced by the amino acid sequence NEHQ.

10. A viral vector according to claim 2, the genome of which comprises a first DNA fragment encoding a non-cleavable and soluble gp160 derived form the natural gp160 of the HIV-1 virus, said non-cleavable and soluble gp160 being different from the natural gp160 in that it does not contain the amino acid sequences KRR and REKR originally found in the natural gp160, and in that the transmembrane region originally found in the natural gp160 is deleted.

11. A viral vector according to claim 10, wherein said non-cleavable and soluble gp160 is different from the natural gp160 in that it comprises a 4-amino acid sequence other than REKR in place of the amino acid sequence REKR originally found in the natural gp160, and a 3-amino acid sequence other than KRR in place of the amino acid sequence KRR originally found in the natural gp160.

12. A viral vector according to claim 11, wherein said non-cleavable and soluble gp160 is different from the natural gp160 in that the amino acid sequences KRR and REKR are replaced respectively by the amino acid sequences QNH and NEHQ.

13. A viral vector according to claim 1, the genome of which comprises a first DNA fragment encoding a non-cleavable gp160 derived form the natural gp160 of the HIV-1 virus, said non-cleavable gp160 being characterized in that it does not contain the amino acid sequence REKR originally found in the natural gp160, and in that the transmembrane region originally found in the natural gp160 is replaced by the transmembrane region of the glycoprotein of the rabies virus.

14. A viral vector according to claim 13, wherein said non-cleavable gp160 is characterized in that it comprises a 4-amino acid sequence other than REKR in place of the amino acid sequence REKR originally found in the natural gp160.

15. A viral vector according to claim 2, the genome of which comprises a first DNA fragment encoding a non-cleavable gp160 derived from the natural gp160 of the HIV-1 virus, said non-cleavable gp160 being characterized in that it does not contain the amino acid sequences KRR and REKR originally found in the natural gp160, and in that the transmembrane region originally found in the natural gp160 is replaced by the transmembrane region of the glycoprotein of the rabies virus.

16. A viral vector according to claim 15, wherein said non-cleavable gp160 is characterized in that it comprises a 4-amino acid sequence other than REKR in place of the amino acid sequence REKR originally found in the natural gp160, and a 3-amino acid sequence other than KRR in place of the amino acid sequence KRR originally found in the natural gp160.

17. A viral vector according to claim 1, the genome of which comprises a first DNA fragment encoding a non-cleavable gp160 derived from the natural gp160 of the HIV-1 virus, said non-cleavable gp160 being characterized in that it does not contain the amino acid sequence REKR originally found in the natural gp160, and in that the amino acid Arg of the transmembrane region originally found in the natural gp160 is replaced by the amino acid Ile.

18. A viral vector according to claim 17, wherein said non-cleavable gp160 is characterized in that it comprises a 4-amino acid sequence other than REKR in place of the amino acid sequence REKR originally found in the natural gp160.

19. A viral vector according to claim 2, the genome of which comprises a first DNA fragment encoding a non-cleavable gp160 derived from the natural gp160 of the HIV-1 virus, said non-cleavable gp160 being characterized in that it does not contain the amino acid sequences KRR and REKR originally found in the natural gp160, and in that the amino acid Arg of the transmembrane region originally found in the natural gp160 is replaced by the amino acid Ile.

20. A viral vector according to claim 19, wherein said non-cleavable gp160 is characterized in that it comprises a 4-amino acid sequence other than REKR in place of the amino acid sequence REKR originally found in the natural gp160, and a 3-amino acid sequence other than KRR in place of the amino acid sequence KRR originally found in the natural gp160.

21. A viral vector according to claim 1, the genome of which comprises a first DNA fragment encoding a non-cleavable gp160 derived from the natural gp160 of the HIV-1 virus, said non-cleavable gp160 being characterized in that it does not contain the amino acid sequence REKR originally found in the natural gp160, and in that the hydrophobic region proximate to the C-terminal end of the REKR sequence as originally found in the natural gp160 is deleted.

22. A viral vector according to claim 2, the genome of which comprises a first DNA fragment encoding a non-cleavable gp160 derived from the natural gp160 of the HIV-1 virus, said non-cleavable gp160 being characterized in that it does not contain the amino acid sequences REKR and KRR originally found in the natural gp160, and in that the hydrophobic region proximate to the C-terminal end of the REKR sequence as originally found in the natural gp160 is deleted.

23. A viral vector according to claim 1, the genome of which comprises a second DNA fragment encoding a signal peptide which is selected from the group consisting of the signal peptide of the precursor of the gp160 of the HIV-1 virus and the signal peptide of the precursor of the glycoprotein of the rabies virus.

24. A viral vector according to claim 2, the genome of which comprises a second DNA fragment encoding a signal peptide which is selected from the group consisting of the signal peptide of the precursor of the gp160 of the HIV-1 virus and the signal peptide of the precursor of the glycoprotein of the rabies virus.

25. A viral vector according to claim 1, the genome of which comprises a functional origin of replication of a poxvirus.

26. A viral vector according to claim 25, the genome of which comprises a functional origin of replication of a vaccinia virus.

27. A viral vector according to claim 2, the genome of which comprises a functional origin of replication of a poxvirus.

28. A viral vector according to claim 27, the genome of which comprises a functional origin of replication of a vaccinia virus.

29. A viral vector according to claim 1, wherein the DNA encoding envelope protein of HIV-1 is encoded by the EcoRI-KpnI and KpnI-HindIII fragments of plasmid PJ19-13, comprising nucleotides 1258 to 1698 of the DNA encoding envelope protein of HIV-1, and the HindIII-XhoI fragment of plasmid PJ19-6, comprising nucleotides 1698 to 9173 of the DNA encoding envelope protein of HIV-1.

30. A viral vector according to claim 2, wherein the DNA encoding envelope protein of HIV-1 is encoded by the EcoRI-KpnI and KpnI-HindIII fragments of plasmid PJ19-13, comprising nucleotides 1258 to 1698 of the DNA encoding envelope protein of HIV-1, and the HindIII-XhoI fragment of plasmid PJ19-6, comprising nucleotides 1698 to 9173 of the DNA encoding envelope protein of HIV-1.

31. A culture of mammalian cells, which is infected with a viral vector as claimed in any one of claims 1 to 6 or 13 to 28.

32. A culture of mammalian cells, which is infected with a viral vector as claimed in any one of claims 7 to 12.

33. A process for producing a non-cleavable and soluble gp160 which comprises recovering said non-cleavable gp160 from a culture of mammalian cells as claimed in claim 32.

* * * * *